(12) United States Patent
Aust et al.

(10) Patent No.: US 9,132,291 B2
(45) Date of Patent: Sep. 15, 2015

(54) WATER-IN-OIL EMULSION COMPOSITIONS CONTAINING GELLAN GUM FOR TOPICAL DELIVERY OF ACTIVE INGREDIENTS TO THE SKIN OR MUCOSA

(75) Inventors: Duncan T. Aust, Huntingdon Valley, PA (US); David P. Jones, San Antonio, TX (US); Aleksa V. Jovanovic, Fort Worth, TX (US); Vitthal Kulkarni, San Antonio, TX (US); Promod Kumar, Mason, OH (US); Lei Shi, Mansfield, TX (US)

(73) Assignee: DFB Technology, Ltd., Fort Worth, TX (US)

( * ) Notice: Subject to any disclaimer, the term of this patent is extended or adjusted under 35 U.S.C. 154(b) by 205 days.

(21) Appl. No.: 13/253,594

(22) Filed: Oct. 5, 2011

(65) Prior Publication Data

US 2012/0149783 A1 Jun. 14, 2012

Related U.S. Application Data

(60) Provisional application No. 61/389,879, filed on Oct. 5, 2010.

(51) Int. Cl.
| | |
|---|---|
| *A61Q 19/00* | (2006.01) |
| *A61K 8/06* | (2006.01) |
| *A61K 8/73* | (2006.01) |
| *A61Q 17/04* | (2006.01) |
| *A61K 9/00* | (2006.01) |

(52) U.S. Cl.
CPC ............... *A61Q 19/00* (2013.01); *A61K 8/064* (2013.01); *A61K 8/73* (2013.01); *A61Q 17/04* (2013.01); *A61K 9/0014* (2013.01); *A61L 2300/402* (2013.01); *A61L 2300/406* (2013.01); *A61L 2300/802* (2013.01)

(58) Field of Classification Search
None
See application file for complete search history.

(56) References Cited

U.S. PATENT DOCUMENTS

| | | | |
|---|---|---|---|
| 3,838,007 | A | 9/1974 | Gerandus van Velzen |
| 4,563,366 | A | 1/1986 | Baird et al. |
| 4,652,441 | A | 3/1987 | Okada et al. |
| 4,822,534 | A | 4/1989 | Lencki et al. |
| 5,041,292 | A | 8/1991 | Feijen |
| 5,332,595 | A | 7/1994 | Gaonkar |
| 5,672,301 | A | 9/1997 | Orly et al. |
| 5,744,337 | A | 4/1998 | Price et al. |
| 5,804,212 | A | 9/1998 | Illum |
| 5,959,073 | A | 9/1999 | Schlameus et al. |
| 6,051,250 | A | 4/2000 | Ribier et al. |
| 6,110,473 | A | 8/2000 | Fitzpatrick et al. |
| 6,471,971 | B1 | 10/2002 | Wollenweber et al. |
| 6,544,503 | B1 | 4/2003 | Vanderhoff et al. |
| 6,685,952 | B1 | 2/2004 | Ma et al. |
| 7,147,885 | B2 | 12/2006 | Asano et al. |
| 2003/0049320 | A1 | 3/2003 | Bhagwatwar et al. |
| 2004/0005283 | A1 | 1/2004 | Cernasov et al. |
| 2005/0042341 | A1 | 2/2005 | Thomas et al. |
| 2005/0118211 | A1 | 6/2005 | Nakamura et al. |
| 2006/0094635 | A1* | 5/2006 | Pereira ........................ 510/470 |
| 2006/0165735 | A1 | 7/2006 | Abril et al. |
| 2007/0026075 | A1 | 2/2007 | Shudo et al. |
| 2007/0042184 | A1 | 2/2007 | Coyne et al. |
| 2007/0104778 | A1 | 5/2007 | Zeng et al. |
| 2008/0299199 | A1 | 12/2008 | Bar-Shalom et al. |
| 2009/0130211 | A1 | 5/2009 | Gamay |
| 2009/0162522 | A1 | 6/2009 | Lai et al. |
| 2009/0275668 | A1 | 11/2009 | Kamishita |
| 2010/0019403 | A1 | 1/2010 | Beco Pinto Reis et al. |
| 2010/0055281 | A1 | 3/2010 | Barrow et al. |
| 2010/0233221 | A1 | 9/2010 | Folmer et al. |
| 2010/0273838 | A1 | 10/2010 | Cui et al. |
| 2011/0091553 | A1 | 4/2011 | Kanaya et al. |
| 2011/0250299 | A1 | 10/2011 | Baseeth et al. |
| 2011/0318321 | A1 | 12/2011 | Selva et al. |

FOREIGN PATENT DOCUMENTS

| | | |
|---|---|---|
| WO | WO9214443 | 9/1992 |
| WO | WO9922768 | 5/1999 |
| WO | WO0191570 A1 | 12/2001 |

OTHER PUBLICATIONS

Patil, et al., Study of Formulation Variables on Properties of Drug-Gellan Beads by Factorial Design, Drug Development and Industrial Pharmacy, pp. 315-326, 2006 (12 pages).

Singh, et al., Effects of Divalent Cations on Drug Encapsulation Efficiency of Deacylated Gellan Gum, Journal of Microencapsulation, pp. 761-771, Nov. 2005 (11 pages).

Agnihotri, et al., Development of Novel Interpenetrating Network Gellan Gum-Poly(vinyl alcohol) Hydrogel Microspheres for the Controlled Release of Carvedilol, Drug and Development and Industrial Pharmacy, pp. 491-503, 2005 (14 pages).

Agnihotri, et al., Controlled Release of Cephalexin through Gellen Gum Beads: Effect of Formulation Parameters on Entrapment Efficiency, Size, and Drug Release, European Journal of Pharmaceutics and Biopharmaceutics 63, pp. 249-261, Mar. 6, 2006 (13 pages).

Nussinovitch, Hydrocolloid Carriers with Filler Inclusion for Diltiazem Hydrochloride Release, Journal of Pharmaceutical Sciences, vol. 96, No. 1, pp. 168-178, Oct. 9, 2006 (11 pages).

Kumar, Nano and Microparticles as Controlled Drug Delivery Devices, Journal of Pharm Pharmaceutical Sciences, 3(2):pp. 234-258, 2000 (24 pages).

Fattah, et al., Physical Characteristics and Release Behavior of Salbutamol Sulfate Beads Prepared with Different Ionic Polysaccharides, Drug and Development and Industrial Pharmacy, 24(6), pp. 541-547, 1998 (7 pages).

(Continued)

*Primary Examiner* — Jeffrey S Lundgren
*Assistant Examiner* — Meghan Finn
(74) *Attorney, Agent, or Firm* — Norton Rose Fulbright US LLP

(57) ABSTRACT

The present invention is directed to water-in-oil (W/O) emulsion compositions containing gellan gum which provide an enhanced rate of release of active ingredients for delivery to the skin or mucosa.

12 Claims, 6 Drawing Sheets

(56) References Cited

OTHER PUBLICATIONS

Kedzierewicz, et al., Effect of the Formulation on the In-Vitro Release of Propranolo from Gellan Beads, International Journal of Pharmaceutica 178, pp. 129-136, 1999 (8 pages).

Alhaique, et al., Gellan in Sustained Release Formulations: Preparation of Gel Capsules and Release Studies, Biomaterials, vol. 17, No. 20, pp. 1981-1986, 1996 (6 pages).

Quigley, et al., Use of Deacetylated Gellan Gum (Gelrite) for the Production of Sulphamethizole Containing Beads, Journal of Microencapsulation, vol. 9, No. 1, pp. 1-7, 1992 (7 pages).

Hashida, et al., An Application of Water-in-Oil and Gelatin-Microsphere-in-Oil Emulsions to Specific Delivery of Anticancer Agent into Stomach Lymphatics, Journal of Phamacokinetics and Biophmarmaceutics, vol. 5, No. 3, pp. 241-255, 1977 (15 pages).

CP Kelco, Gellan Gum for Pharmaceutical Applications, www.cpkelco.com, PH-12, pp. 1-6, 1997 (6 pages).

CP Kelco, Gellan Gum Gel (G3), www.cpkelco.com, PH-14, pp. 1-4, 1997 (4 pages).

Shimoadacki-cho, et al., Prolonged Release of Bleomycin from Parenteral Gelatin Sphere-in-Oil-in-Water Multiple Emulsions, Cheml Pharm. Bulletin, vol. 30, pp. 1408-1415, 1982 (8 pages).

Hashida, et al., Evaulation of Water in Oil and Microsphere in Oil Emulsions as a Specific Delivery System of 5-Fluorouracil into Lymphatics, Chem. Pharm. Bulletin, vol. 25, pp. 2410-2418, 1977 (9 pages).

Hashida, et al., Dosage Form Characteristics of Microsphere-in-Oil Emulsion. II: Examination of Some Factors Affecting Lymphotropicity, Chemical and Pharmaceutical Bulletin, vol. 28, No. 6, pp. 1659-1666, Jun. 1980 (8 pages).

Healthpoint, Ltd., AAPS Poster:The Enhanced Release of Active Molecules of Water-in-Oil Emulsions Containing Gellan Gum, Nov. 8, 2009 (1 page).

Jovanovic, et al., AAPS Abstract, The Enhanced Release of Active Molecules of Water-in-Oil Emulsions Containing Gellan Gum, Healthpoint, Ltd., Nov. 11, 2009 (1 page).

* cited by examiner

WATER-IN-OIL EMULSION COMPOSITIONS CONTAINING GELLAN GUM FOR TOPICAL DELIVERY OF ACTIVE INGREDIENTS TO THE SKIN OR MUCOSA

CROSS REFERENCE TO RELATED APPLICATIONS

This application claims priority to U.S. Provisional Patent Application No. 61/389,879, filed Oct. 5, 2010, which is incorporated by reference in its entirety.

BACKGROUND OF THE INVENTION

1. Field of the Invention

The present invention relates generally to topical water-in-oil (W/O) emulsion compositions containing gellan gum which provide an enhanced rate of release of active ingredients for delivery to the skin or mucosa.

2. Background

Topical formulations generally have to combine multiple, and sometimes competing, attributes, such as those relating to aesthetics, stability, delivery and compatibility. In regard to aesthetics, topical formulations are generally required to display appropriate tactile and visual properties when applied to the skin or mucosa, while often also maintaining functionality in regard to delivery of various active ingredients onto or into the skin or mucosa.

Emulsions are widely used as topical formulations for the delivery of active ingredients, including drug and cosmetic active ingredients, to the skin or mucosa. Emulsions are generally made by preparing separate hydrophobic and hydrophilic phases and mixing the two together, usually with one or more emulsifying agents (surfactants), which reduce the surface tension between the immiscible phases creating micelles, i.e., a surfactant effect, thereby making the dispersion physically stable. The two basic types of such dispersions usually comprise 1) an oil-in-water type emulsion (O/W), which is a dispersed hydrophobic phase in a continuous aqueous phase; and 2) a water-in-oil type emulsion (W/O), which is a dispersed aqueous phase in a continuous hydrophobic phase.

The rate of release of active ingredients from a composition onto the skin or mucosa can be an important aspect of treatment. An enhanced (increased) rate of release of active ingredients can give quick relief to conditions such as infections, pruritus (itching), or pain.

SUMMARY OF THE INVENTION

The present invention is directed to topical water-in-oil (W/O) emulsion compositions containing gellan gum which provide an enhanced rate of release of active ingredients for delivery to the skin or mucosa of a human or animal.

In one aspect of the present invention, there is disclosed a composition comprising a surfactant; a continuous hydrophobic phase; and a dispersed aqueous phase comprising water, an active ingredient, a cation, and gellan gum; wherein the composition is a water-in-oil emulsion. In one embodiment, the active ingredient is water soluble. In another embodiment, the surfactant is in the hydrophobic phase. In still another embodiment, the surfactant is in the aqueous phase. In various embodiments, the cation is selected from the group consisting of calcium ($Ca^{2+}$), magnesium ($Mg^{2+}$), sodium ($Na^+$), potassium ($K^+$), and hydrogen ions ($H^+$), and mixtures thereof. The source of the cation can be a salt or acid. In one embodiment, the cation is sodium ($Na^+$). In another embodiment the source of the sodium cation ($Na^+$) is sodium chloride.

In another aspect, there is disclosed a method of topically delivering an active ingredient to the skin or mucosa comprising applying to the skin or mucosa a composition comprising a surfactant; a continuous hydrophobic phase; and a dispersed aqueous phase comprising water, the active ingredient, a cation, and gellan gum; wherein the composition is a water-in-oil emulsion. In one embodiment, the active ingredient is water soluble. In another embodiment, the surfactant is in the hydrophobic phase. In still another embodiment, the surfactant is in the aqueous phase. In various embodiments, the cation is selected from the group consisting of calcium ($Ca^{2+}$), magnesium ($Mg^{2+}$), sodium ($Na^+$), potassium ($K^+$), and hydrogen ions ($H^+$), and mixtures thereof. The source of the cation can be a salt or acid. In one embodiment, the cation is sodium ($Na^+$). In another embodiment the source of the sodium cation ($Na^+$) is sodium chloride.

Unless otherwise specified, the percent values expressed herein are weight by weight and are in relation to the total composition.

The term "active ingredient" means a drug or cosmetic agent directed to enhancing, modifying or maintaining a biological or physiological functionality.

The use of the word "a" or "an" when used in conjunction with the term "comprising" or "containing" in the claims and/or the specification may mean "one," but it is also consistent with the meaning of "one or more," "at least one," and "one or more than one."

Throughout this application, the term "about" is used to indicate that a value includes the inherent variation of error for the device obtaining the value, the method being employed to determine the value, or the variation that exists among the objects being evaluated.

The use of the term "or" in the claims is used to mean "and/or" unless explicitly indicated to refer to alternatives only or the alternatives are mutually exclusive, although the disclosure supports a definition that refers to only alternatives and "and/or,"

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any embodiment of any of the present apparatuses and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
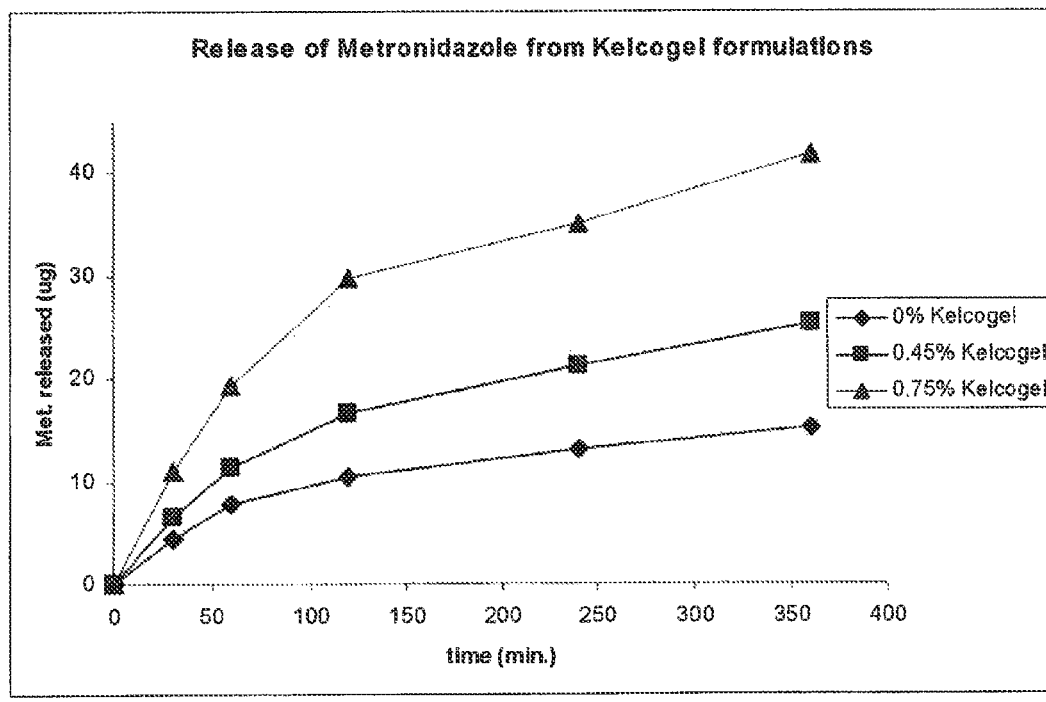
FIG. 1 Plot of the release of metronidazole from sample formulations with varying gellan gum levels over time.

One aspect of the present invention provides for a composition comprising a surfactant; a continuous hydrophobic phase; and a dispersed aqueous phase comprising water, an active ingredient, a cation, and gellan gum; wherein the composition is a water-in-oil emulsion. In one embodiment, the active ingredient is water soluble.

It was surprisingly found that in the water-in-oil emulsion formulations of the present invention, the rate of release of the active ingredient increased (was faster) with increased concentrations of gellan gum. The rate of release of the active ingredient in a formulation with gellan gum was also surprisingly higher (faster) than the rate of release of the active ingredient in a formulation without gellan gum. This is an unexpected phenomenon. When the emulsion cools during manufacture, the gellan gum will congeal the dispersed aqueous phase droplets forming gel-like solid beads dispersed within the continuous hydrophobic phase. The active ingredient is bound in the matrix of the gel-like beads (dispersed aqueous phase). As the concentration of gellan gum in the formulation increases, the strength of the gel matrix will also increase which should bind the active ingredient even further. Thus, it would be expected that the rate of release of the active ingredient would decrease (be slower) as the concentration of gellan gum increased. However, in the present invention, surprisingly the rate of release of the active ingredient increased (was enhanced) with increased concentration of gellan gum.

Microscopic review of the formulations indicates that the active ingredient crystallizes in the dispersed aqueous phase when gellan gum is present in the formulation. Without being bound to any theory, the applicants postulate that the unusual release behavior may be due to the swelling (water uptake) effect of the gellan gum in the aqueous phase making the apparent concentration of the active ingredient higher.

Another aspect of the present invention provides for a method of topically delivering an active ingredient comprising applying the composition of the invention to the skin or mucosa of a human or animal. The desired rate of release of the active ingredient can be controlled by selection of the concentration of gellan gum in the composition, i.e. compositions with higher concentrations of gellan gum will give higher (faster) rates of release of active ingredients.

The compositions of the present invention are particularly suitable for topical delivery of anesthetics, analgesics, antibiotics, antimicrobials, and other active ingredients where the desired rate of release of the active ingredient can be selected.

Topical Compositions

The topical compositions of the present invention comprise a surfactant; a continuous hydrophobic phase; and a dispersed aqueous phase comprising water, an active ingredient, a cation, and gellan gum; wherein the composition is a water-in-oil emulsion. The surfactant may be in the continuous hydrophobic phase or the dispersed aqueous phase.

Gellan Gum

Gellan gum is an exocellular heteropolysaccharide produced by microbial fermentation of *Sphingomonas elodea*. The polymer backbone consists of glucose, glucuronic acid, and rhamnose in the molar ratio of 2:1:1. These are linked together to give a primary structure consisting of a linear tetrasaccharide repeat unit. Gellan gum is available commercially from CP Kelco under the trademarks KELCOGEL® and GELRITE®. Gellan gum is available in two types, low acyl and high acyl content; and in a variety of industrial, food, cosmetic, and pharmaceutical grades.

Gellan gum forms aqueous thermally set gels with cations including calcium ($Ca^{2+}$), magnesium ($Mg^{2+}$), sodium ($Na^+$), potassium ($K^+$), or hydrogen ions ($H^+$). The gelling mechanism involves cation-induced intermolecular chain association. The cations promote helix formation and subsequent aggregation. Typical ranges of cations in the formulations of the present invention are generally from about 0.016% w/w to about 2% w/w depending on which cation is used. For example, 0.016% calcium cation ($Ca^{2+}$) and 0.5% sodium cation ($Na^+$) (equivalent to about 1.3% sodium chloride) form optimal gels (see CP Kelco Data Sheet PH-12, "Gellan Gum for Pharmaceutical Applications", 1997). In one embodiment, 0.5% w/w sodium chloride is used. These effects are dependent on the cations involved and the temperature of the system. Aqueous gels are prepared by hydrating gellan gum in hot water with a cation (from a salt or acid) followed by cooling. Gelation occurs upon cooling below the setting temperature. The setting temperature is controlled by the cation valency and concentration. Upon reheating, the gellan gum gels will melt. The characteristics of the gel can be controlled by selection of the gellan gum type and concentration, cation type and concentration, and pH of the system.

Typical ranges of gellan gum in the formulations of the present invention are generally from about 0.05% w/w to about 5% w/w; or from about 0.05% w/w to about 4% w/w; or from about 0.05% w/w to about 3% w/w; or from about 0.05% w/w to about 2.5% w/w; or from about 0.05% w/w to about 2% w/w; or from about 0.05% w/w to about 1.5% w/w; or from about 0.05% w/w to about 1% w/w; or from about 0.05% w/w to about 0.75% w/w; or from about 0.1% w/w to about 0.75% w/w; or from about 0.15% w/w to about 0.75% w/w; or from about 0.2% w/w to about 0.75% w/w; or from about 0.25% w/w to about 0.75% w/w; or from about 0.3% w/w to about 0.75% w/w; or from about 0.35% w/w to about 0.75% w/w; or from about 0.4% w/w to about 0.75% w/w; or from about 0.45% to about 0.75% w/w.

Surfactants

Surfactants or combinations of surfactants capable of forming water-in-oil emulsions are suitable for the present invention. These surfactants serve as emulsifiers. Non-limiting examples include sorbitan sesquioleate (ARLACEL® 83); and polyglyceryl-4 isostearate (and) cetyl PEG/PPG-10/1 dimethicone (and) hexyl laurate (ABIL® WE09). The surfactant may be added to the hydrophobic phase or the aqueous phase in the present invention.

Active Ingredients

Active ingredients, defined as drug or cosmetic agents directed to enhancing, modifying or maintaining a biological or physiological functionality, are suitable for the present invention. In one embodiment of the invention, the active ingredient is water soluble. More than one active ingredient may be used in the present invention. Non-limiting examples of active ingredients suitable for the present invention include anti-acne agents, e.g., metranidazole, salicylic acid and clindamycin phosphate; analgesics, e.g., sodium salicylate and doxepin HCl; anesthetics, e.g., lidocaine HCl, pramoxine HCl, tetracaine HCl, and dibucaine HCl; antihistamines, e.g. diphenhydramine HCl and doxepin HCl; antibiotics, e.g., sodium sulfacetamide, mupirocin, and tetracycline HCl; antifungals, e.g., butenafine HCl, miconazole nitrate, undecylenic acid, and naftifine HCl; antivirals, e.g. acyclovir and penciclovir; antimicrobials, e.g., benzalkonium chloride, chlorhexidine gluconate, ethylhexylglycerin, gentamicin sulfate, povidone iodine, PVP iodine, triclosan, and benzethonium chloride; antipruritics, e.g., doxepin HCl, allantoin, pramoxine HCl, and zinc acetate; skin protectants, e.g., allantoin, glycerin, and zinc acetate; enzymes, e.g. collagenase, papain, trypsin and subtilisin; keratolytics, e.g. salicylic acid and dichloroacetic acid; sunscreens, e.g., PABA and benzophenone.

Hydrophobic Continuous Phase

Suitable components of the hydrophobic continuous phase include, but are not limited to, one or more plant, animal, paraffinic, and synthetically derived fats, butters, greases, waxes, solvents, and oils. These include, but are not limited to, mineral oils, vegetable oils, water insoluble organic esters, water insoluble glycerides, non-volatile silicones, volatile silicones, and fluorinated compounds. Plant derived materials include, but are not limited to, arachis (peanut) oil, balsam Peru oil, carnauba wax, candellila wax, castor oil, hydrogenated castor oil, cocoa butter, coconut oil, corn oil, cotton seed oil, jojoba oil, macadamia seed oil, olive oil, orange oil, orange wax, palm kernel oil, rapeseed oil, safflower oil, sesame seed oil, shea butter, soybean oil, sunflower seed oil, tea tree oil, vegetable oil, and hydrogenated vegetable oil. Non-limiting examples of animal derived materials include beeswax, cod liver oil, emu oil, lard, mink oil, shark liver oil, squalane, squalene, and tallow. Non-limiting examples of paraffinic materials include isoparaffin, microcrystalline wax, heavy mineral oil, light mineral oil, ozokerite, petrolatum, white petrolatum, and paraffin. A non-limiting example of a non-volatile silicone is dimethicone. A non-limiting example of a volatile silicone is cyclomethicone. Non-limiting examples of water insoluble organic esters include C12-15 alkyl benzoate, isopropyl myristate, and isopropyl palmitate. A non-limiting example of water insoluble glycerides includes caprylic/capric triglyceride. A non-limiting example of a fluorinated compound is polytetrafluoroethylene (PTFE).

Dispersed Aqueous Phase

The dispersed aqueous phase comprises water, an active ingredient, a cation, and gellan gum. The cation can be selected from the group consisting of calcium ($Ca^{2+}$), magnesium ($Mg^{2+}$), sodium ($Na^+$), potassium ($K^+$), and hydrogen ions ($H^+$), and mixtures thereof. The source of the cation can be a salt or acid. In one embodiment, the cation is sodium ($Na^+$). In another embodiment the source of the sodium cation ($Na^+$) is sodium chloride. More than one active ingredient may be used in the present invention. In one embodiment, the active ingredient is water soluble. More than one cation may be used in the present invention. Additional water soluble ingredients may be added to the aqueous phase.

Additional Ingredients

The compositions of the present invention can include additional ingredients known in the art that are suitable for topical compositions of this nature. Non-limiting examples include absorbents, deodorizers, additional surfactants, solvents, rheology modifiers, film formers, stabilizers, stabilizers, emollients, moisturizers, humectants, preservatives, antimicrobials, antioxidants, chelating agents, fragrances, and colorants. Non-limiting examples of preservatives include benzyl alcohol and methylparaben. Non-limiting examples of humectants include glycerin and propylene glycol.

Manufacturing Process

The compositions of the present invention can be prepared by techniques and methods known by one of ordinary skill in the art. The composition can be prepared by the following method in any order: 1) Preparing an aqueous phase by dissolving the active ingredient, cation source (from a salt or acid), and gellan gum in water, and heating the aqueous phase to a temperature suitable for emulsification. 2) Preparing a hydrophobic phase by combining and heating the hydrophobic phase ingredients to a temperature suitable for emulsification. 3) Adding a surfactant to either the aqueous phase or the hydrophobic phase. 4) Admixing the aqueous phase with the hydrophobic phase to form a water-in-oil emulsion. 5) Cooling the emulsion to room temperature. Other methods for making water-in-oil emulsions known by one of ordinary skill in the art can be employed.

These compositions can be prepared using processing equipment known by one of ordinary skill in the art, e.g. blenders, mixers, mills, homogenizers, dispersers, dissolvers, etc.

The compositions of the present invention can be packaged in any package suitable for dispensing a topical composition. The compositions can be packaged in multi-use, single-dose, or metered dose packages. Non-limiting examples include a tube, bottle, jar, pump container, pressurized container, bladder container, aerosol container, aerosol spray container, non-aerosol spray container, syringe, pouch, or sachet.

In-Vitro Release Test

The release of active ingredients, including lidocaine HCl metronidazole, and allantoin, from the exemplified formulations was determined utilizing a Franz Cell diffusion apparatus. A 0.45 um Durapore HVLP membrane was used between the donor and receptor compartments. The receptor fluid used for analysis of lidocaine HCl was 0.2M $NaH_2PO_4$/EtOH/SDS (69/30/1). The receptor fluid used for analysis of metronidazole was 600 mL Ethanol (USP) and 400 mL Phosphate Buffer (1.3 g $Na_2HPO_4$ and 1.5 g $KH_2PO_4$). The receptor fluid used for analysis of allantoin was 10 mM $KH_2PO_4$ buffer (pH=4.7). The sampling of the receptor fluid was performed at 0.5, 1, 2, 4 and 6 hours at 35° C. The concentration of the released actives in the collected samples of the receptor fluid was determined by HPLC analysis. The HPLC mobile phase used for analysis of lidocaine HCl was 0.2M $NaH_2PO_4$/EtOH/SDS (69/30/1). The HPLC mobile phase used for analysis of metronidazole was 600 mL Ethanol (USP) and 400 mL Phosphate Buffer (1.3 g $Na_2HPO_4$ and 1.5 g $KH_2PO_4$). The HPLC mobile phase used for analysis of allantoin was ACN/Water (90/10).

EXAMPLES

The following examples are included to demonstrate certain non-limiting aspects of the invention. It should be appreciated by those of skill in the art that the techniques disclosed in the examples which follow represent techniques discovered by the applicants to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Metronidazole Formulations

TABLE 1

| Ingredient | Formula A (0% Gellan Gum) % w/w | Formula B (0.45% Gellan Gum) % w/w | Formula C (0.75% Gellan Gum) % w/w |
|---|---|---|---|
| Gellan Gum (Kelcogel ® CG-LA) | 0.0 | 0.45 | 0.75 |
| Metronidazole | 0.75 | 0.75 | 0.75 |
| White Petrolatum | 53.5 | 53.5 | 53.5 |
| Sorbitan Sesquioleate | 5.0 | 5.0 | 5.0 |
| Sodium Chloride | 0.5 | 0.5 | 0.5 |
| Glycerin | 5.0 | 5.0 | 5.0 |
| Benzyl Alcohol | 0.15 | 0.15 | 0.15 |
| Water | q.s. to 100% | q.s. to 100% | q.s. to 100% |

Formulas A, B, and C in Table 1 above were prepared as follows:

The aqueous phase was prepared by combining metronidazole, gellan gum, sodium chloride, and glycerin in water and heating to 65° C. to 75° C. with mixing until dissolved.

The hydrophobic phase was prepared by combining white petrolatum, sorbitan sesquioleate, and benzyl alcohol while heating to 65° C. to 75° C. with mixing until melted and uniform.

The hydrophobic and aqueous phases were combined with mixing and mixed for 15 minutes forming an emulsion. The emulsion was mixed and allowed to cool to 35° C. at which time mixing was discontinued and the emulsion was allowed to cool to room temperature.

Figure 2:
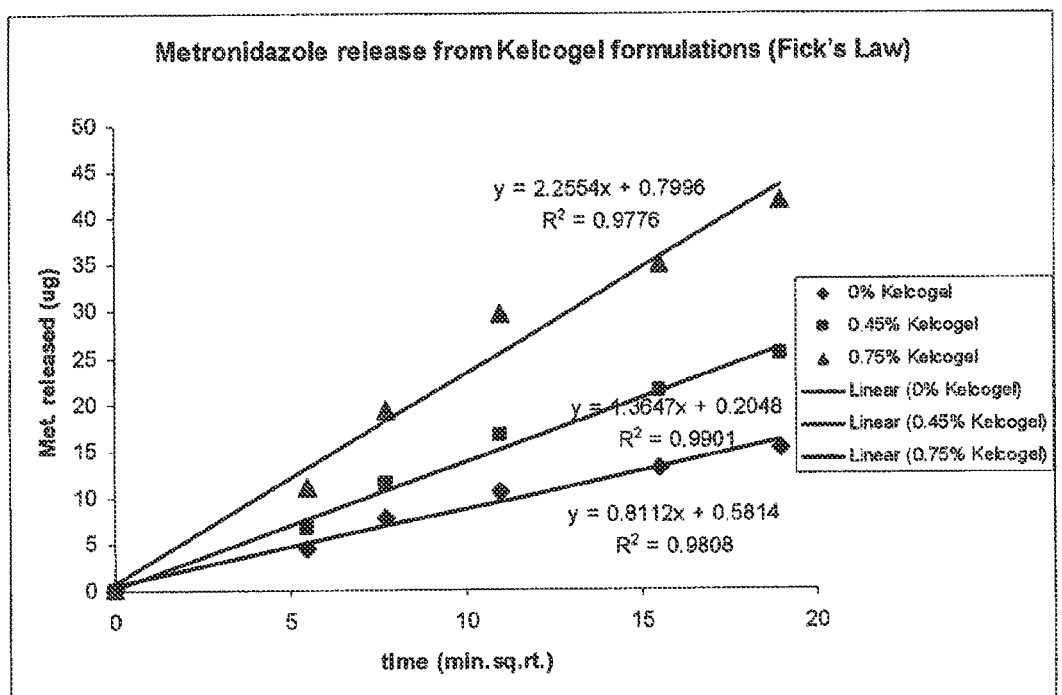
FIG. 2 Plot of the release of metronidazole from sample formulations with varying gellan gum levels over the square root of time (Fick's law of diffusion).

The results of the in-vitro release study are in FIG. 1 and FIG. 2. As can be seen by the plots, the rate of release of metronidazole increased as the concentration of gellan gum increased.

Example 2

Allantoin Formulations

TABLE 2

| Ingredient | Formula D (0% Gellan Gum) % w/w | Formula E (0.45% Gellan Gum) % w/w | Formula F (0.75% Gellan Gum) % w/w |
|---|---|---|---|
| Gellan Gum (Kelcogel ® CG-LA) | 0.0 | 0.45 | 0.75 |
| Allantoin | 0.1 | 0.1 | 0.1 |
| White Petrolatum | 53.5 | 53.5 | 53.5 |
| Sorbitan Sesquioleate | 5.0 | 5.0 | 5.0 |
| Sodium Chloride | 0.5 | 0.5 | 0.5 |
| Glycerin | 5.0 | 5.0 | 5.0 |
| Benzyl Alcohol | 0.15 | 0.15 | 0.15 |
| Water | q.s. to 100% | q.s. to 100% | q.s. to 100% |

Formulas D, E, and F in Table 2 above were prepared as follows:

The aqueous phase was prepared by combining allantoin, gellan gum, sodium chloride, and glycerin in water and heating to 70° C. to 80° C. with mixing until dissolved.

The hydrophobic phase was prepared by combining white petrolatum, sorbitan sesquioleate, and benzyl alcohol while heating to 70° C. to 80° C. with mixing until melted and uniform.

The hydrophobic and aqueous phases were combined with mixing and mixed for 10 minutes forming an emulsion. The emulsion was mixed and allowed to cool to room temperature.

Figure 3:
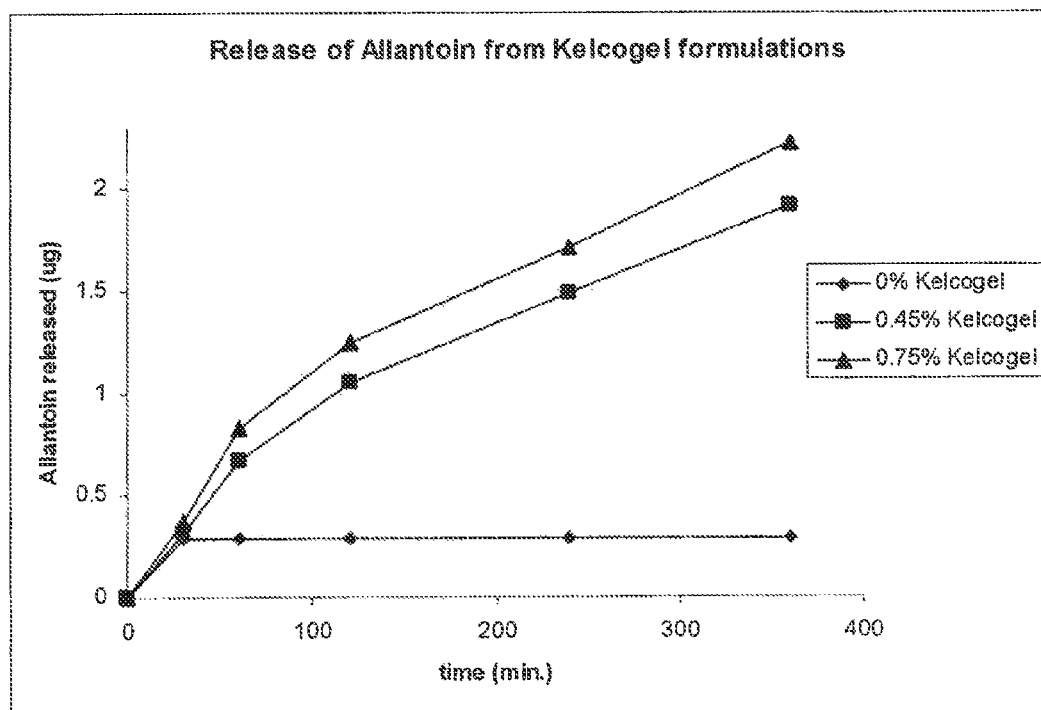
FIG. 3 Plot of the release of allantoin from sample formulations with varying gellan gum levels over time.
Figure 4:
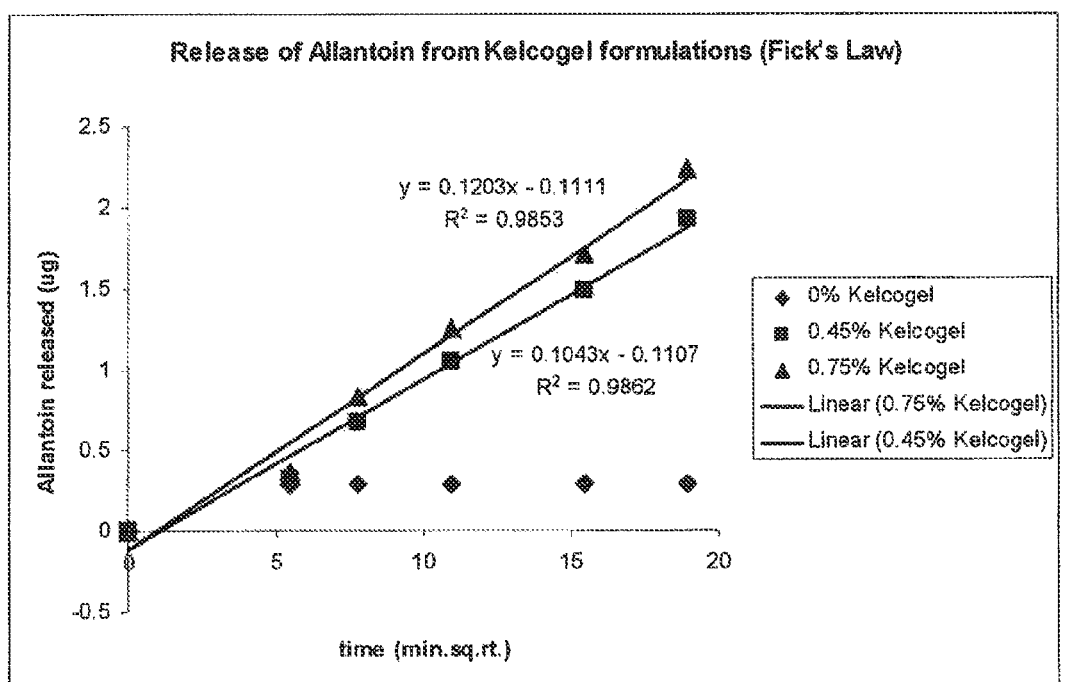
FIG. 4 Plot of the release of allantoin from sample formulations with varying gellan gum levels over the square root of time (Fick's law of diffusion).

The results of the in-vitro release study are in FIG. 3 and FIG. 4. As can be seen by the plots, the rate of release of allantoin increased as the concentration of gellan gum increased.

Example 3

Lidocaine HCl Formulations

TABLE 3

| Ingredient | Formula G (0% Gellan Gum) % w/w | Formula H (0.45% Gellan Gum) % w/w | Formula I (0.75% Gellan Gum) % w/w |
|---|---|---|---|
| Gellan Gum (Kelcogel ® CG-LA) | 0.0 | 0.45 | 0.75 |
| Lidocaine HCl | 2.0 | 2.0 | 2.0 |
| White Petrolatum | 53.5 | 53.5 | 53.5 |
| Sorbitan Sesquioleate | 5.0 | 5.0 | 5.0 |
| Sodium Chloride | 0.5 | 0.5 | 0.5 |
| Glycerin | 5.0 | 5.0 | 5.0 |
| Benzyl Alcohol | 0.15 | 0.15 | 0.15 |
| Water | q.s. to 100% | q.s. to 100% | q.s. to 100% |

Formulas G, H, and I in Table 3 above were prepared as follows:

The aqueous phase was prepared by combining lidocaine HCl, gellan gum, sodium chloride, and glycerin in water and heating to 70° C. to 80° C. with mixing until dissolved.

The hydrophobic phase was prepared by combining white petrolatum, sorbitan sesquioleate, and benzyl alcohol while heating to 70° C. to 80° C. with mixing until melted and uniform.

The hydrophobic and aqueous phases were combined with mixing and mixed for 10 minutes forming an emulsion. The emulsion was mixed and allowed to cool to room temperature.

Figure 5:
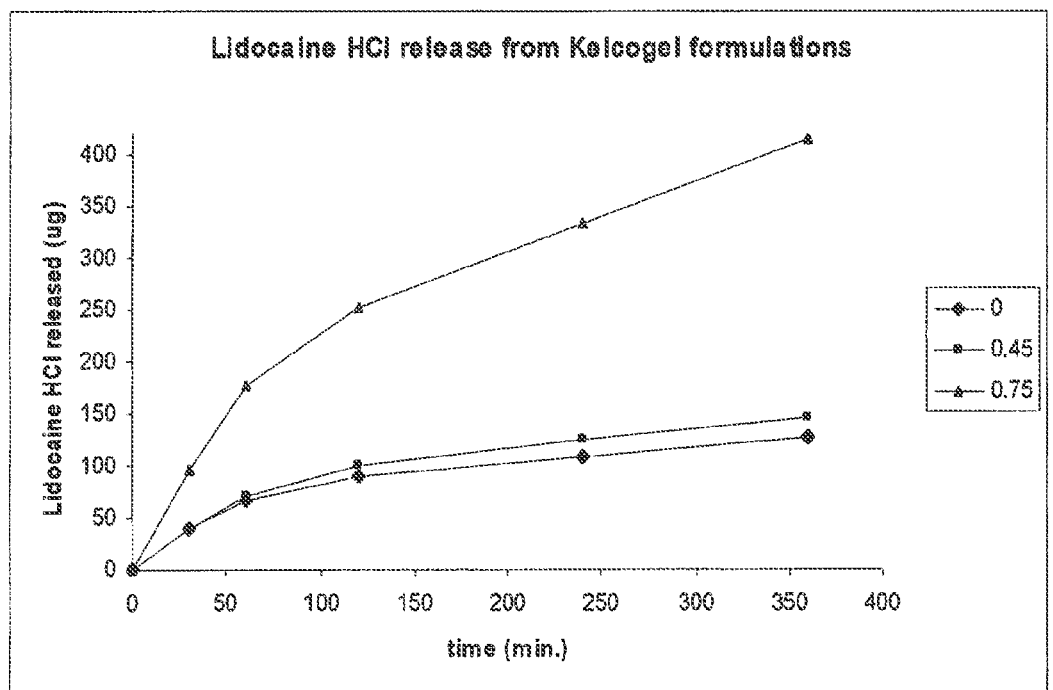
FIG. 5 Plot of the release of lidocaine HCl from sample formulations with varying gellan gum levels over time.
Figure 6:
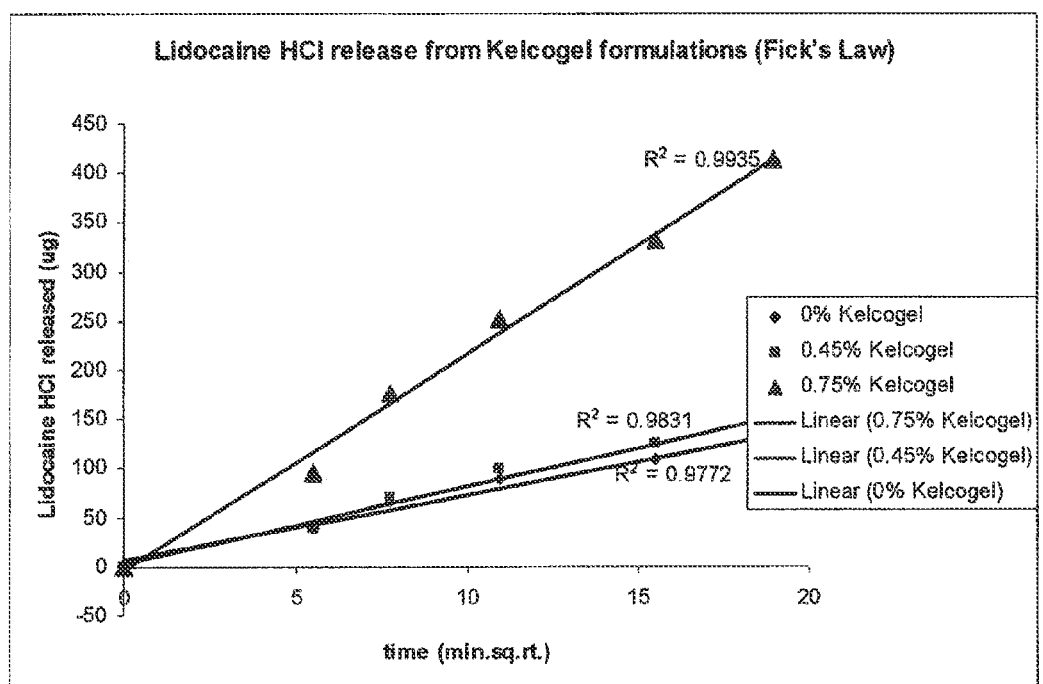
FIG. 6 Plot of the release of lidocaine HCl from sample formulations with varying gellan gum levels over the square root of time (Fick's law of diffusion).

The results of the in-vitro release study are in FIG. 5 and FIG. 6. As can be seen by the plots, the rate of release of lidocaine HCl increased as the concentration of gellan gum increased.

The invention claimed is:

1. A topical composition comprising: a surfactant; a continuous hydrophobic phase; and a dispersed aqueous phase comprising water, a water-soluble active ingredient, a cation, and gellan gum; wherein the composition is a water-in-oil emulsion; and wherein the rate of release of the water-soluble active ingredient from the composition increases with increasing concentration of gellan gum as demonstrated in-vitro with a Franz Cell diffusion apparatus.

2. The composition of claim 1, wherein the cation is selected from the group consisting of calcium ($Ca^{2+}$), magnesium ($Mg^{2+}$), sodium ($Na^+$), potassium ($K^+$), and hydrogen ions ($H^+$), and mixtures thereof.

3. The composition of claim 2, wherein the cation is sodium (Na$^+$).

4. The composition of claim 2, wherein the source of the cation is a salt or acid.

5. The composition of claim 3, wherein the source of the sodium (Na$^+$) is sodium chloride.

6. A method of topically delivering a water-soluble active ingredient to the skin or mucosa comprising: applying to the skin or mucosa a composition comprising a surfactant; a continuous hydrophobic phase; and a dispersed aqueous phase comprising water, the water-soluble active ingredient, a cation, and gellan gum; wherein the composition is a water-in-oil emulsion; and wherein the rate of release of the water-soluble active ingredient to the skin or mucosa increases with increasing concentration of gellan gum.

7. The method of claim 6, wherein the cation is selected from the group consisting of calcium (Ca$^{2+}$), magnesium (Mg$^{2+}$), sodium (Na$^+$), potassium (K$^+$), and hydrogen ions (H$^+$), and mixtures thereof.

8. The method of claim 7, wherein the cation is sodium (Na$^+$).

9. The method of claim 7, wherein the source of the cation is a salt or acid.

10. The method of claim 8, wherein the source of the sodium (Na$^+$) is sodium chloride.

11. A method of providing an enhanced rate of release of a water-soluble active ingredient from a topical composition for delivery to the skin or mucosa comprising: adding gellan gum to the composition; wherein the composition comprises: a surfactant; a continuous hydrophobic phase; and a dispersed aqueous phase comprising water, the water-soluble active ingredient, and a cation; wherein the composition does not contain gellan gum; wherein the composition is a water-in-oil emulsion; and wherein the gellan gum is added to the dispersed aqueous phase.

12. The method of claim 11, wherein the rate of release of the water-soluble active ingredient is further enhanced comprising: increasing the concentration of gellan gum in the dispersed aqueous phase; wherein the enhanced rate of release correlates to the increased concentration of gellan gum.

* * * * *